United States Patent [19]

Prevost et al.

[11] Patent Number: 5,837,204

[45] Date of Patent: Nov. 17, 1998

[54] SYSTEM FOR DISINFECTING THE WATER LINES OF A DENTAL UNIT

[75] Inventors: André Prevost; Jean Barbeau, both of Montréal; Ludger Cote, Matane; Robert Charland, Boucherville; Gary Savage, Montréal; Michel Swift, Outremont, all of Canada

[73] Assignees: Universite de Montreal; Theratechnologies, Inc., both of Montreal, Canada

[21] Appl. No.: 844,249

[22] Filed: Apr. 18, 1997

Related U.S. Application Data

[62] Division of Ser. No. 189,434, Jan. 31, 1994.
[51] Int. Cl.$^6$ ................... A61L 2/26; B08B 9/06; A61G 13/00
[52] U.S. Cl. ................. 422/105; 134/166 C; 134/169 C; 137/511; 210/136; 422/28; 422/117; 433/80
[58] Field of Search ..................... 210/101, 136, 210/141, 198.1, 651; 134/22.1, 22.11, 22.12, 166 C, 166 R, 169 C, 169 R; 422/28, 33, 37, 41, 105, 116, 117; 433/80, 104, 82; 137/15, 240, 511

[56] References Cited

U.S. PATENT DOCUMENTS

| | | | |
|---|---|---|---|
| 3,481,689 | 12/1969 | Rosdahl et al. . | |
| 3,811,408 | 5/1974 | Thompson | 118/73 |
| 4,545,956 | 10/1985 | Ciszewski et al. | 422/28 |
| 4,695,385 | 9/1987 | Boag | 210/636 |
| 4,752,444 | 6/1988 | Bowen et al. | 422/28 |
| 5,147,605 | 9/1992 | Tatsuno et al. | 422/37 |
| 5,147,613 | 9/1992 | Heilmann et al. | 422/116 |
| 5,158,454 | 10/1992 | Viebahn et al. | 433/82 |

(List continued on next page.)

FOREIGN PATENT DOCUMENTS

| | | |
|---|---|---|
| 0 111 249 | 6/1984 | European Pat. Off. . |
| 0 233 847 | 8/1987 | European Pat. Off. . |
| 0 317 521 | 5/1989 | European Pat. Off. . |

OTHER PUBLICATIONS

*Control of Bacteria In Dental Water Supplies*, Douglas, van Noort, British Dental Journal—Mar. 6, 1993, pp. 167–174.
*Reduction of Microbial Contamination in Dental Units with Povidone–Iodine 10*, Lauderdale, Mayhew, JADA vol. 113 pp. 230–234, Aug. 1986.
*The Effect of Chlorohexidine on Streptococcus Sanguis Biofilms*, Millward, Wilson Microbios 5B, pp. 155–164, 1988.
"Reduction of microbial contamination in dental units with povidone–iodine 10%" S.E. Mills, P.W. Lauderdale, R.B. Mayhew, JADA, vol. 113, Aug. 1986, pp. 280–284.

(List continued on next page.)

*Primary Examiner*—Joseph W. Drodge
*Attorney, Agent, or Firm*—Merchant, Gould, Smith, Welter, and Schmidt

[57] ABSTRACT

A system for disinfecting the water lines of a dental unit is provided with first and second unidirectional check valves. Water at a first pressure is normally supplied to the water lines of the dental unit through the first check valve. A reservoir of liquid disinfectant can be pressurized at a second pressure higher than the first pressure by the air compressor already equipping the dental unit to supply disinfectant to the water lines of the dental unit through the second check valve. Liquid disinfectant is prevented from reaching the water supply line by the first check valve. In the same manner, when the reservoir is not pressurized, the second check valve prevents water from the water supply line from reaching the disinfectant. The reservoir is formed with an upper neck and a bottom, and the disinfecting system is provided with a housing on which an upper stopper fitting into the neck and a lower reservoir bottom support are mounted, whereby for mounting the reservoir on the housing, one successively tilts the reservoir, places the neck on the stopper and slides the reservoir bottom on the support, which sliding movement is facilitated by a rounded edge of the reservoir bottom.

9 Claims, 3 Drawing Sheets

U.S. PATENT DOCUMENTS

| | | | |
|---|---|---|---|
| 5,167,201 | 12/1992 | Peles | 119/14.18 |
| 5,178,830 | 1/1993 | Riera Aixala | 422/37 |
| 5,204,004 | 4/1993 | Johnston et al. | 210/651 |
| 5,234,832 | 8/1993 | Disch et al. | 435/264 |
| 5,308,579 | 5/1994 | Melon et al. | 422/28 |
| 5,318,443 | 6/1994 | Overmyer | 433/104 |
| 5,360,338 | 11/1994 | Waggoner | 433/80 |
| 5,526,841 | 6/1996 | Detsch et al. | 137/15 |

OTHER PUBLICATIONS

"The effect of chlorhexidine on *Streptococcus sanguis* biofilms" A. Millward, M. Wilson, Microbios, 1989, pp. 155–164.

"Control of bacteria in dental water supplies" C.W.I. Douglas, R. van Noort, British Dental Journal, Mar. 1993, pp. 167–173.

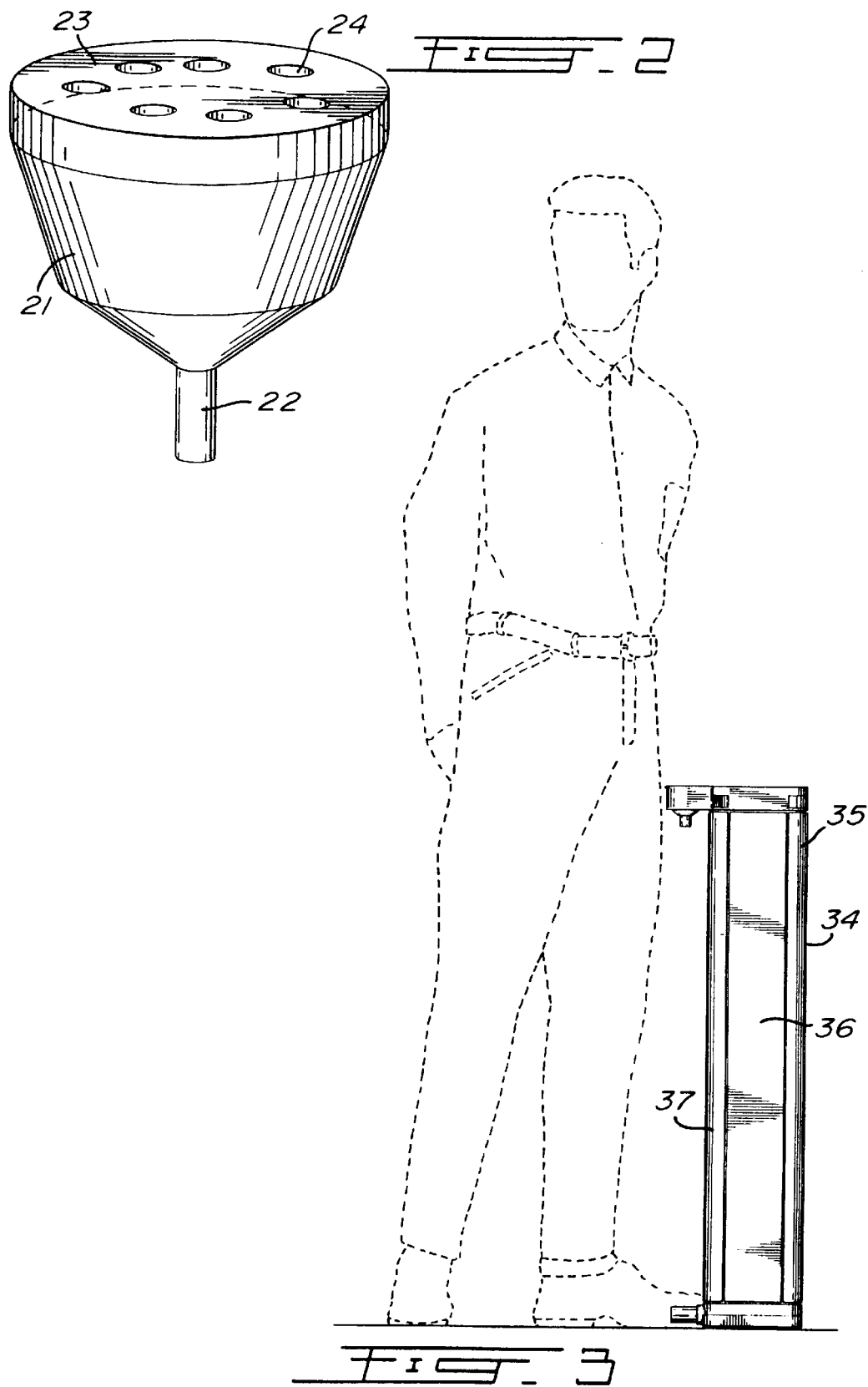

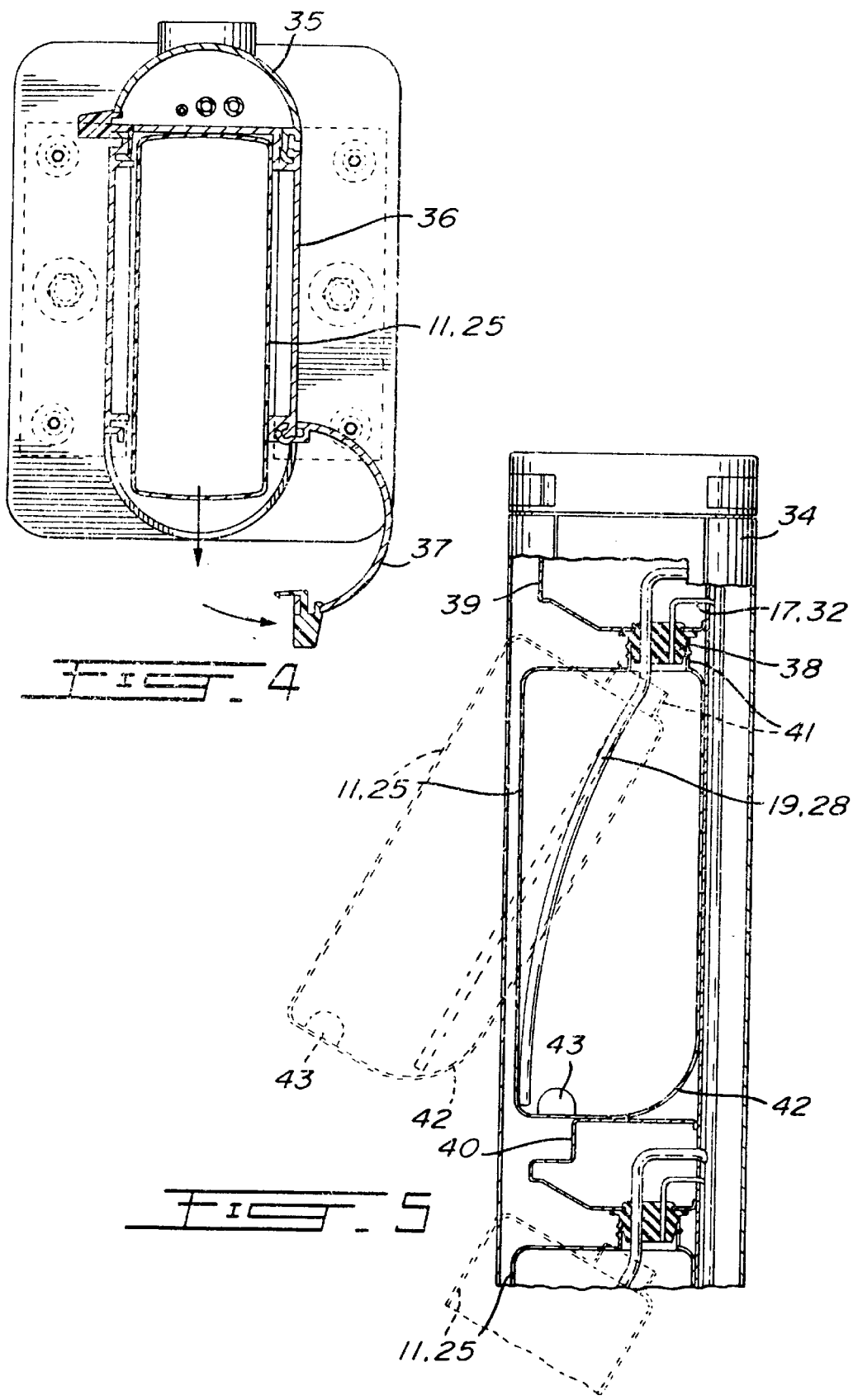

SYSTEM FOR DISINFECTING THE WATER LINES OF A DENTAL UNIT

This is a Divisional of application Ser. No. 08/189,434, filed Jan. 31, 1994, which application is incorporated herein by reference.

BACKGROUND OF THE INVENTION

1. Field of the Invention

The present invention relates to a system to be mounted to a new or already installed dental unit for disinfecting the water lines thereof.

2. Brief Description of the Prior Art

As well known to those of ordinary skill in the art, a bacterial film, called "biofilm" develops in the network of small diameter water lines of a dental unit, which network supplying the handpieces and water/air syringe with water. This biofilm attach to the inner walls of the water lines. After some weeks, this film is visible to the naked eye.

When water flows in the water lines, a great quantity of bacteria detach from the biofilm. These bacteria, in suspension in the water, are projected directly in the mouth of the patient and are present in the aerosols produced by the handpieces. Studies have indicated that water from the handpieces and air/water syringe of a dental unit does not meet with the microbiological standards of public health regarding drinking water. Such concentration of bacteria, even of non-pathogenic bacteria, constitutes a potential problem of infection for immuno-deficient patients.

OBJECTS OF THE INVENTION

An object of the present invention is therefore to provide a system capable of efficiently disinfecting the water lines of a dental unit, in view of disrupting the biofilm formed therein.

SUMMARY OF THE INVENTION

More specifically, in accordance with the present invention, there is provided a system for disinfecting water lines of a dental unit, comprising:

first valve means;

means for supplying water at a first pressure to the water lines of the dental unit through the first valve means; and means actuated for supplying liquid disinfectant to the water lines of the dental unit at a second pressure higher than the first pressure.

According to the invention, the first valve means comprises means responsive to the difference between the first and second pressures to prevent disinfectant from reaching the water supplying means.

In accordance with preferred embodiments of the present invention, the first valve means comprises a unidirectional check valve. Also the disinfectant supplying means may comprise a reservoir for storing the liquid disinfectant, this reservoir being pressurized at the second pressure by an air compressor already equipping the dental unit. Moreover, the disinfectant from the reservoir is preferably supplied to the water lines of the dental unit through a second unidirectional check valve whereby, when the reservoir is not pressurized, that second check valve prevents water from the water supplying means to reach the reservoir of disinfectant. The reservoir advantageously comprises an upper neck and a bottom, and the disinfecting system a housing on which an upper stopper fitting into the neck and a lower reservoir bottom support means are mounted, whereby for mounting the reservoir on the housing, one successively tilts the reservoir, places the neck on the stopper and slides the reservoir bottom on the support means, which sliding movement is facilitated by a rounded edge of the reservoir bottom.

Finally, the system for disinfecting water lines of a dental unit may comprises a second reservoir in which clean water is stored, and means for pressurizing this water reservoir at the second pressure for supplying clean water to the lines of the dental unit through a third unidirectional check valve when supply of water from the water supplying means is interrupted or when water from the water supplying means is contaminated.

The objects, advantages and other features of the present invention will become more apparent upon reading of the following non restrictive description of a preferred embodiment thereof, given by way of example only with reference to the accompanying drawings.

BRIEF DESCRIPTION OF THE DRAWINGS

In the appended drawings:

FIG. 2 is a funnel of the disinfecting system according to the present invention;

FIG. 3 is an elevational view of a vertical housing in which the disinfecting system of the present invention is enclosed;

FIG. 4 is a horizontal cross sectional view of the housing of FIG. 3 enclosing a reservoir of liquid disinfectant; and FIG. 5 is an elevational, partly cross sectional view of the vertical housing of FIG. 3, showing how the reservoir of disinfectant is installed and removed from the housing.

DETAILED DESCRIPTION OF THE PREFERRED EMBODIMENT

Figure 1:
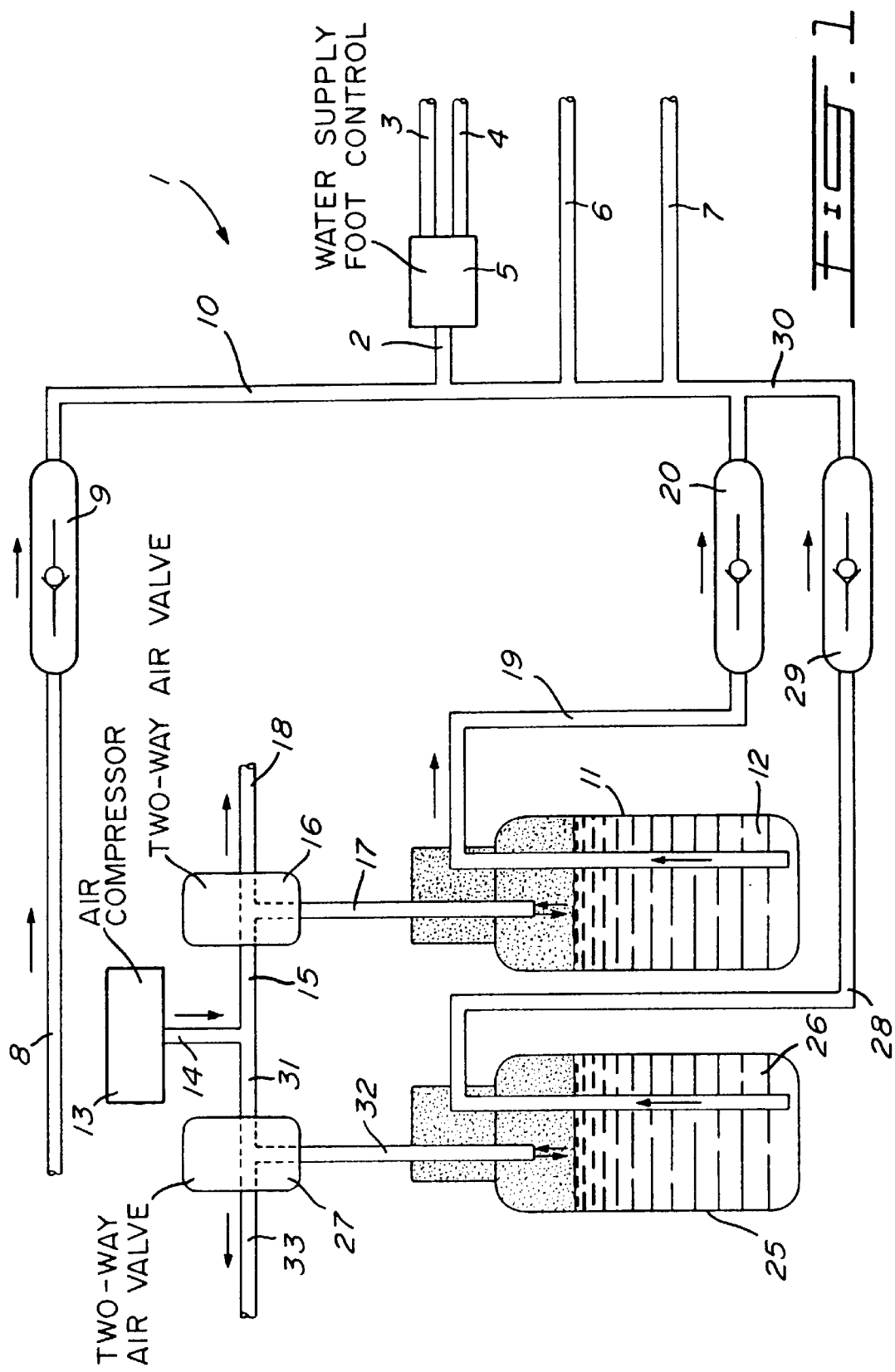
FIG. 1 is a schematic diagram showing the structure of the system according to the present invention, for disinfecting the water lines of a dental unit.

The system in accordance with the present invention, for disinfecting the water lines of a dental unit is generally identified by the reference 1 in FIG. 1 of the appended drawings.

As illustrated in FIG. 1, the water lines of a dental unit (not shown) generally comprise:

a water line 2 connected to a foot control 5 for supplying water to dental handpieces through water lines 3 and 4;

a water line 6 for supplying an air/water dental syringe (not shown): and a water line 7 for supplying a unit (not shown) for automatically filling a water glass.

As shown in FIG. 1, the water lines 2, 6 and 7 are themselves supplied with fresh water through a water supply line 8, a unidirectional check valve 9, and a water line 10. The pressure in the water supply line 8 is, for example, 45 psi. More specifically, fresh water is supplied (a) to the foot control 5 through line 8, valve 9, and lines 10 and 2, (b) to the water glass filling unit through line 8, valve 9, and lines 10 and 7, and (c) to the air/water dental syringe through line 8, valve 9, and lines 10 and 6.

The system 1 in accordance with the present invention, for disinfecting the water lines of a dental unit further comprises a reservoir 11 for containing liquid disinfectant 12, and a two-way air valve 16 which can be mechanical or electro-mechanical.

A dental unit conventionally comprises a compressor 13 for supplying the dental handpieces and syringe with pressurized air. This already available compressor 13 will also be used to supply pressurized air at a pressure of, for example, 55 psi to the reservoir 11 to supply liquid disinfectant to lines 2, 6 and 7 through a line 19 and a unidirectional check valve 20.

More specifically, in a first position of the two-way air valve 16, pressurized air from the compressor 13 is supplied to the reservoir 11 through air lines 14 and 15, valve 16 and air line 17. In a second position of valve 16, pressurized air in reservoir 11 is evacuated through line 17, valve 16 and air line 18.

Disinfection of the water lines such as 2–4, 6 and 7 of the dental unit is advantageously carried out at the end of the day's work. The user first turns the control valve 16 from its second position in which it is normally positioned, to its first position to supply pressurized air at 55 psi from the compressor 13 to the reservoir 11. The user then activates successively or simultaneously the foot control 5, the dental syringe (not shown) and the water glass filling unit (not shown) whereby disinfectant 12 will flow from the reservoir 11 through line 19, check valve 20, and lines 2, 3, 4, 6 and 7 to reach the dental handpieces and syringe, and the water glass filling unit. As pressure of the disinfectant (55 psi) is higher than pressure of water (45 psi) in the water supply line 8, check valve 9 prevents disinfectant from reaching supply line 8. Preferably, the liquid disinfectant 12 is colored to allow the user to see when disinfectant flows from the dental handpieces and syringe and from the water glass filling unit. The water lines of the dental unit are then full of disinfectant whereby the foot control 5, the dental syringe and the water glass filling unit can be turned off. The two-way air valve 16 is turned back to its second position to stop supply of pressurized air to the reservoir 11. Pressurized air from the reservoir 11 is then evacuated through lines 17 and 18, and valve 16. Finally, the water, air and electric supplies of the dental unit are switched off as normally done at the end of the day's work.

The day after, the water, air and electric supplies of the dental unit are switched on. The foot control 5, dental syringe and water glass filling unit are then turned on to evacuate disinfectant 12 from the water lines of the dental unit. As the reservoir 11 is no longer supplied with pressurized air from compressor 13, water is allowed to flow from supply line 8 through the check valve 9 and lines 2, 3, 4, 6 and 7, but is prevented from reaching the reservoir 11 by the action of check valve 20. Evacuation of the disinfectant is completed when the liquid from the handpieces, syringe and water glass filling unit is no longer colored. The dental unit can then be operated as usual.

To facilitate the use of the disinfecting system 1 of the present invention, a funnel 21 illustrated in FIG. 2 is used. Funnel 21 comprises a narrow end formed with a cylindrical tube 22 that can be readily mounted on the suction apparatus (not shown) of the dental unit to prevent formation of contaminated aerosols. Funnel 21 also comprises a wider end 23 including a plurality of openings such as 24 to receive the outlet tubes of the handpieces, dental syringe, water glass filling unit, etc. or the free end of the water lines thereof. Funnel 21 is preferably made of translucent plastic material to enable the user to see the color of the liquid flowing therein.

The system 1 in accordance with the present invention, for disinfecting the water lines of a dental unit further comprises a reservoir 25 for containing clean water 26, and a two-way air valve 27 which can be mechanical or electromechanical. The already available compressor 13 will supply pressurized air at a pressure of 55 psi to the reservoir 25 to supply clean water to lines 2, 6 and 7 through a water line 28, a unidirectional check valve 29, and a water line 30.

More specifically, in a first position of the two-way air valve 27, pressurized air from the compressor 13 is supplied to the reservoir 25 through air lines 14 and 31, valve 27 and air line 32. In a second position of valve 16, pressurized air in reservoir 25 is evacuated through line 32, valve 27 and air line 33.

When water from the supply line 8 is contaminated or supply of water from line 8 is interrupted, one has only to turn valve 27 from its second position in which it is normally positioned, to its first position to supply pressurized air at 55 psi from the compressor 13 to the reservoir 11. Clean water from reservoir 25 is then supplied to the lines 2, 6 and 7 through water line 28, check valve 29 and water line 30 whereby the dentist or dentist assistant can continue to use the dental handpieces and syringe, and the water glass filling unit. As pressure in the reservoir 25 (55 psi) is higher than pressure of water (45 psi) in the water supply line 8, check valve 9 prevents clean water 26 from reservoir 25 from reaching supply line 8.

When the supply of water from line 8 is reestablished, the two-way air valve 27 is turned back to its second position to stop supply of pressurized air to the reservoir 25. Pressurized air from the reservoir 25 is then evacuated through lines 32 and 33, and valve 27.

Alternatively, reservoir 25 may also contain liquid disinfectant as reservoir 11.

As illustrated in FIG. 3, the system 1 in accordance with the present invention is advantageously enclosed in a housing 34 presenting the shape of a hollow column generally oval in cross section (FIG. 4). Column 34 can be easily mounted in the proximity of a dentist's chair (not shown) in the region of the water and air connections. Obstruction caused by the disinfecting system 1 of the invention is thereby minimized.

As shown in FIGS. 3 and 4, housing 34 is formed of three extrusions 35, 36 and 37. Outer extrusion 37 is hinged on central extrusion 36 whereby housing 34 can be opened to install the reservoirs 11 and 25 therein.

A generally conical stopper 38, made of flexible plastic material, is fixedly mounted in the housing 34. More specifically, stopper 38 is mounted on a support 39, made of sheet metal secured to the inside of extrusion 36. Stopper 38 is traversed by line 17,32 for supplying pressurized air to the reservoir 11,25, and by line 19,28 for supplying liquid from that reservoir 11,25. Line 19,28 is flexible and extends downwardly from stopper 38 to reach the bottom of reservoir 11,25.

The reservoir 11,25 is advantageously made of plastic material. It presents the general shape of a parallelepiped and is formed with an upper cylindrical neck 41 dimensioned to fit on stopper 38. The bottom of reservoir 11,25 has a rounded edge 42 and is formed with cavities such as 43.

A support 40, made of sheet metal and secured to the inside of central extrusion 36 receives the bottom of reservoir 11,25.

Therefore, to install a reservoir 11,25 in the housing 34, this reservoir 11,25 is tilted and neck 41 placed around stopper 38. The bottom of reservoir 11,25 is then pushed inside housing 34 to slide onto support 40. The bottom of reservoir 11,25 is then applied to the support 40 and neck 41 tightly sealed by stopper 38. Extrusion 37 is finally pivoted to close housing 34 whereby reservoir 11,25 is held in place in that housing. As can be appreciated, rounded edge 42 facilitates insertion of a full reservoir 11,25 in the housing 34, while cavities 43 makes manual removal of an empty reservoir 11,25 easier.

As shown in FIG. 5, the two reservoirs 11, 25 are superposed and are mounted in housing 34 in the same way.

The reservoirs 11 and 25 and/or the housing 34 are preferably opaque to prevent light to pass through them and possibly deactivate the disinfectant. Advantageously, the reservoirs 11 and 25 will be opaque with a thin elongate and vertical translucent window enabling visual inspection of the level of disinfectant in the reservoirs.

When the dental unit of the dentist and the dental unit of the dentist's assistant have a common water supply, only one disinfecting system 1 in accordance with the present invention is required.

Also, the disinfecting system 1 of the present invention must be installed upstream the vinyl water lines of the dental unit in which the biofilm grows.

Finally, it should be pointed out that the disinfectant is applied when the dental unit is not in function, so that no disinfectant is released during dental treatment.

Although the present invention has been described hereinabove by way of a preferred embodiment thereof, this embodiment can be modified at will, within the scope of the appended claims, without departing from the spirit and nature of the subject invention.

What is claimed is:

1. A water line disinfecting system for disinfecting water lines of a dental unit, said water lines to be connected to a source of water at a first pressure, comprising:

a first unidirectional valve device for establishing a first unidirectional connection from the source to the water lines whereby water at the first pressure from the source is supplied to the water lines through the first unidirectional valve device;

a reservoir of liquid disinfectant;

a second unidirectional valve device for establishing a second unidirectional connection from the reservoir of liquid disinfectant to the water lines;

means for pressurizing the reservoir of liquid disinfectant at a second pressure higher than the first pressure in order to supply the liquid disinfectant from the reservoir to the water lines through the second unidirectional valve device;

wherein the first unidirectional valve device comprises means responsive to the difference between the first and second pressures for preventing the liquid disinfectant supplied to the water lines from reaching the source and wherein, when the reservoir of liquid disinfectant is not pressurized, the second unidirectional valve device comprises means responsive to the first pressure for preventing the water supplied to the water lines from reaching the reservoir; and wherein the reservoir of liquid disinfectant comprises an upper neck and a bottom, and wherein said water line disinfecting system further comprises a housing on which an upper stopper fitting into said neck and a lower reservoir bottom support means are mounted, whereby for mounting the reservoir of liquid disinfectant on said housing, one successively tilts said reservoir, places said neck on said stopper and slides said reservoir bottom on said support means.

2. A water line disinfecting system as recited in claim 1, in which the bottom of the reservoir of liquid disinfectant is formed with a rounded edge to facilitate sliding of said bottom on the support means.

3. A water line disinfecting system for disinfecting water lines of a dental unit, said water lines to be connected to a source of water at a first pressure, comprising:

a first unidirectional valve device for establishing a first unidirectional connection from the source to the water lines whereby water at the first pressure from the source is supplied to the water lines through the first unidirectional valve device;

a reservoir of liquid disinfectant;

a second unidirectional valve device for establishing a second unidirectional connection from the reservoir of liquid disinfectant to the water lines;

means for pressurizing the reservoir of liquid disinfectant at a second pressure higher than the first pressure in order to supply the liquid disinfectant from the reservoir to the water lines through the second unidirectional valve device;

wherein the first unidirectional valve device comprises means responsive to the difference between the first and second pressures for preventing the liquid disinfectant supplied to the water lines from reaching the source and wherein, when the reservoir of liquid disinfectant is not pressurized, the second unidirectional valve device comprises means responsive to the first pressure for preventing the water supplied to the water lines from reaching the reservoir;

a second reservoir in which clean water is stored;

a third unidirectional valve device for establishing a third unidirectional connection from the second reservoir to the water lines;

means for pressurizing the second reservoir at a third pressure higher than the first pressure to supply the clean water from the second reservoir to the water lines of the dental unit when supply of the water from the source is interrupted or when water from the source is contaminated; and wherein, when the second reservoir is not pressurized, the third unidirectional valve device comprises means responsive to the first pressure or the second pressure for preventing the water from the source or the liquid disinfectant supplied to the water lines from reaching the second reservoir.

4. A water line disinfecting system as recited in claim 3, in which said means for pressurizing the second reservoir comprises an air compressor already equipping the dental unit.

5. A water line disinfecting system as recited in claim 3, in which said third unidirectional valve device comprises a unidirectional check valve.

6. A water line disinfecting system as recited in claim 3, wherein the second reservoir comprises an upper neck and a bottom, and wherein said water line disinfecting system further comprises a housing on which an upper stopper fitting into said neck and a lower reservoir support means are mounted, whereby, for mounting the second reservoir on said housing, one successively tilts the second reservoir, places the neck onto said stopper and slides the reservoir bottom on said support means.

7. A water line disinfecting system as recited in claim 6, in which said bottom of the second reservoir comprises a rounded edge to facilitate sliding of said bottom on the support means.

8. A water line disinfecting system for disinfecting water lines of a dental unit, said water lines to be connected to a source of water at a first pressure, comprising:

a first unidirectional valve device for establishing a first unidirectional connection from the source to the water lines whereby water at the first pressure from the source is supplied to the water lines through the first unidirectional valve device;

a reservoir of liquid disinfectant;

a second unidirectional valve device for establishing a second unidirectional connection from the reservoir of liquid disinfectant to the water lines;

means for pressurizing the reservoir of liquid disinfectant at a second pressure higher than the first pressure in order to supply the liquid disinfectant from the reservoir to the water lines through the second unidirectional valve device;

wherein the first unidirectional valve device comprises means responsive to the difference between the first and second pressures for preventing the liquid disinfectant supplied to the water lines from reaching the source and wherein, when the reservoir of liquid disinfectant is not pressurized, the second unidirectional valve device comprises means responsive to the first pressure for preventing the water supplied to the water lines from reaching the reservoir; and wherein the reservoir of liquid disinfectant is a first reservoir, and wherein said water line disinfecting system further comprises:
- a second reservoir in which liquid disinfectant or clean water is stored;
- means for pressurizing said second reservoir at a third pressure higher than the first pressure to supply the liquid disinfectant or the clean water from said second reservoir to the water lines of the dental unit;
- a housing formed of a hollow column; and
- means for superposing said first and second reservoirs in said hollow column.

9. A water line disinfecting system for disinfecting water lines of a dental unit, said water lines to be connected to a source of water at a first pressure, comprising:

a first unidirectional valve device for establishing a first unidirectional connection from the source to the water lines whereby water at the first pressure from the source is supplied to the water lines through the first unidirectional valve device;

a reservoir of liquid disinfectant;

a second unidirectional valve device for establishing a second unidirectional connection from the reservoir of liquid disinfectant to the water lines;

means for pressurizing the reservoir of liquid disinfectant at a second pressure higher than the first pressure in order to supply the liquid disinfectant from the reservoir to the water lines through the second unidirectional valve device;

wherein the first unidirectional valve device comprises means responsive to the difference between the first and second pressures for preventing the liquid disinfectant supplied to the water lines from reaching the source and wherein, when the reservoir of liquid disinfectant is not pressurized, the second unidirectional valve device comprises means responsive to the first pressure for preventing the water supplied to the water lines from reaching the reservoir;

means for supplying the liquid disinfectant from the water lines to a suction apparatus already equipping the dental unit; and wherein said means for supplying the liquid disinfectant from the water lines to the suction apparatus comprises a funnel means.

* * * * *